(12) United States Patent
Yokoyama et al.

(10) Patent No.: US 7,003,074 B2
(45) Date of Patent: *Feb. 21, 2006

(54) STRESS MEASUREMENT METHOD USING X-RAY DIFFRACTION

(75) Inventors: Ryouichi Yokoyama, Tachikawa (JP); Kamihisa Endo, Saitama (JP)

(73) Assignee: Rigaku Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/069,447

(22) Filed: Feb. 28, 2005

(65) Prior Publication Data

US 2005/0190880 A1 Sep. 1, 2005

Related U.S. Application Data

(63) Continuation of application No. 10/650,059, filed on Aug. 27, 2003, now Pat. No. 6,874,369.

(30) Foreign Application Priority Data

Aug. 30, 2002 (JP) ............... 2002-255766

(51) Int. Cl.
  *G01N 23/20* (2006.01)
  *G01D 7/02* (2006.01)
(52) U.S. Cl. .................... 378/72; 378/73; 73/800
(58) Field of Classification Search .......... 378/70–73, 378/81–85, 208; 73/800, 786, 787, 789
See application file for complete search history.

(56) References Cited

U.S. PATENT DOCUMENTS

| 3,639,758 | A | | 2/1972 | Shimura |
| 4,095,103 | A | | 6/1978 | Cohen et al. |
| 4,128,762 | A | | 12/1978 | Nagao et al. |
| 4,489,425 | A | | 12/1984 | Borgonovi |
| 4,561,062 | A | | 12/1985 | Mitchell |
| 4,686,631 | A | | 8/1987 | Ruud |
| 4,800,580 | A | * | 1/1989 | Houtman et al. ............. 378/71 |
| 5,272,746 | A | | 12/1993 | Isobe et al. |
| 5,414,747 | A | * | 5/1995 | Ruud et al. ................... 378/73 |

(Continued)

FOREIGN PATENT DOCUMENTS

DE        197 19 473 A1    4/1998

OTHER PUBLICATIONS

Lappalainen J. et al., "Electrical and Mechanical Properties of Ferroelectric Thin Films Laser Ablated from a PBO. 97NDO.02 (ZRO.55T10.45)03 Target" Journal of Applied Physics, American Institute of Physics. New York, US, vol. 82, No. 7, pp. 3469-3477, XP000738070, ISSN: 0021-8979, Oct. 1, 1997.

(Continued)

*Primary Examiner*—Edward J. Glick
*Assistant Examiner*—Irakli Kiknadze
(74) *Attorney, Agent, or Firm*—Frishauf, Holtz, Goodman & Chick, P.C.

(57) ABSTRACT

A stress of a c-axis-oriented specimen of a tetragonal polycrystal is measured using X-ray diffraction under the assumption of a plane stress state. An X-ray optical system is set in the location of $\phi=0°$, 45° or 90°. An X-ray diffracted at a crystal plane (the direction of the normal thereto is the direction of an angle of $\psi$) with the Miller indices (hkl) is detected. A diffraction angle $\theta$ in a strain state is measured in the vicinity of a Bragg's angle $\theta_0$ in a non-strain state. Strains $\epsilon$ with respect to a plurality of $\psi$ are calculated from the difference between the measurement values $\theta$ and the Bragg's angle $\theta_0$. Specific stress calculation formulae are determined with respect to the tetragonal system having the Laue symmetry 4/mmm. The stress is calculated from the slope of the linear line of plotted measurement results.

2 Claims, 18 Drawing Sheets

P: SPECIMEN COORDINATE SYSTEM
X: CRYSTAL COORDINATE SYSTEM
L: LABORATORY COORDINATE SYSTEM

U.S. PATENT DOCUMENTS

| | | | | |
|---|---|---|---|---|
| 5,848,122 | A | * | 12/1998 | Kurtz ........................... 378/80 |
| 6,058,160 | A | * | 5/2000 | Kurtz ........................... 378/70 |
| 6,156,623 | A | | 12/2000 | Hendrix et al. |
| 6,514,835 | B1 | | 2/2003 | Hendrix et al. |
| 6,874,369 | B1 | * | 4/2005 | Yokoyama et al. ........... 73/789 |

OTHER PUBLICATIONS

Tanaka et al., "X-ray residual stress measurement of aluminum thin films with 111 fiber texture" Journal of the Society of Materials Science, Japan, Soc. Mater. Sci. Japan, Japan, vol. 45, No. 10, pp. 1138-1144, XP00902646, ISSN: 0514-5163, Oct. 1996.

Tanaka, K. et al., "A Method of X-Ray Stress Management for Cubic Polycrystals With Fiber Texture", J. Soc. Mat. Sci., Japan, vol. 45, No. 8, pp. 945-950, Aug., 1996.

Tanaka, K. et al., "Elastic Constants and X-Ray Stress Measurement of Cubic Thin Films With Fiber Texture", JSME International Journal, Series A, vol. 42, No. 2, pp. 224-234, 1998.

Tanaka, K. et al., "X-Ray Stress Management of Hexagonal Polycrystals With [001] Fiber Texture", JSME International Journal, Series A, vol. 41, No. 2, pp. 287-289, 1998.

Jikkenbutsurigaku kouza 20, X-sen kaisetsu (Experimental physics course 20, x-ray diffraction), edited by K. Kohra, Kyoritsu Shuppan Co., Ltd., 1998, pp. 571-575, "16.2 x-sen ouryokusokuteino genri (Principle of X-ray stress measurement)".

X-sen kesshoukaisekino tebiki, Ouyoubutsurigaku sensho (Guide to X-ray Crystal Analysis, Applied Physics Sampler), T. Sakurai, Shokabou, 1983, p. 53.

Takao Hanabusa et al: Japanese Standard for X-Ray Stress Measurement, pp. 181-188; IOM Communications Ltd., London, U.K., Jun. 2000.

* cited by examiner

FIG. 2

$$\lambda = 2d \sin \theta \quad \cdots (1)$$

$\lambda$ : X-RAY WAVELENGTH d : LATTICE SPACING $\theta$ : BRAGG'S DIFFRACTION ANGLE $$\frac{\partial d}{d} = -\cot \theta \, \partial \theta \quad \cdots (2)$$

$$\varepsilon = \frac{d - d_0}{d_0} \quad \cdots (3)$$

$\varepsilon$ : STRAIN $d_0$ : LATTICE SPACING IN NON-STRAIN STATE $$\varepsilon = -\cot \theta_0 \, (\theta - \theta_0) \quad \cdots (4)$$

P: SPECIMEN COORDINATE SYSTEM

X: CRYSTAL COORDINATE SYSTEM

L: LABORATORY COORDINATE SYSTEM

FIG. 5

|  | S | σ | ε |
|---|---|---|---|
| CRYSTAL COORDINATE SYSTEM | $S_{ijkl}$ | $\sigma^{*}_{ij}$ | $\varepsilon^{*}_{ij}$ |
| SPECIMEN COORDINATE SYSTEM | $S^{P}_{ijkl}$ | $\sigma_{ij}$ | $\varepsilon_{ij}$ |
| LABORATORY COORDINATE SYSTEM | $S^{L}_{ijkl}$ | $\sigma^{L}_{ij}$ | $\varepsilon^{L}_{ij}$ |

S: ELASTIC COMPLIANCE CONSTANT

σ: STRESS

ε: STRAIN

FIG. 6

ELASTIC COMPLIANCE CONSTANT IN TENSOR NOTATION $S_{ijkl}$ (i, j, k, l = 1, 2, 3)

↕ RELATIONSHIP

6×6 MATIRIX IN MATRIX NOTATION $S_{pq}$ (p, q = 1, 2, 3, 4, 5, 6)

| ij kl | 11 | 22 | 33 | 23 | 32 | 13 | 31 | 12 | 21 |
|---|---|---|---|---|---|---|---|---|---|
| p q | 1 | 2 | 3 | 4 | 4 | 5 | 5 | 6 | 6 |

|  | p = 1, 2, 3 | p = 4, 5, 6 |
|---|---|---|
| q = 1, 2, 3 | $S_{ijkl} = S_{pq}$ | $S_{ijkl} = \frac{1}{2} S_{pq}$ |
| q = 4, 5, 6 | $S_{ijkl} = \frac{1}{2} S_{pq}$ | $S_{ijkl} = \frac{1}{4} S_{pq}$ |

FIG. 7

$$\pi = R3(-\beta) \quad \cdots (5)$$

$$\omega = R2(-\psi)R3(-\phi) \quad \cdots (6)$$

$$\gamma = \omega\pi \quad \cdots (7)$$

$$R1(\delta) = \begin{pmatrix} 1 & 0 & 0 \\ 0 & \cos\delta & -\sin\delta \\ 0 & \sin\delta & \cos\delta \end{pmatrix} \quad \cdots (8)$$

$$R2(\delta) = \begin{pmatrix} \cos\delta & 0 & \sin\delta \\ 0 & 1 & 0 \\ -\sin\delta & 0 & \cos\delta \end{pmatrix} \quad \cdots (9)$$

$$R3(\delta) = \begin{pmatrix} \cos\delta & -\sin\delta & 0 \\ \sin\delta & \cos\delta & 0 \\ 0 & 0 & 1 \end{pmatrix} \quad \cdots (10)$$

$$\varepsilon^L_{33} = \gamma_{3i}\,\gamma_{3j}\,\varepsilon^*_{ij} \quad \cdots (11)$$

$$\varepsilon^*_{ij} = S_{ijkl}\,\sigma^*_{kl} \quad \cdots (12)$$

$$\sigma^*_{kl} = \pi_{pk}\,\pi_{ql}\,\sigma_{pq} \quad \cdots (13)$$

$$\varepsilon^L_{33} = \gamma_{3i}\,\gamma_{3j}\,S_{ijkl}\,\pi_{pk}\,\pi_{ql}\,\sigma_{pq} \quad \cdots (14)$$

FIG. 8

TETRAGONAL SYSTEM WITH LAUE SYMMETRY 4/mmm $$S = \begin{bmatrix} S_{11} & S_{12} & S_{13} & 0 & 0 & 0 \\ S_{12} & S_{11} & S_{13} & 0 & 0 & 0 \\ S_{13} & S_{13} & S_{33} & 0 & 0 & 0 \\ 0 & 0 & 0 & S_{44} & 0 & 0 \\ 0 & 0 & 0 & 0 & S_{44} & 0 \\ 0 & 0 & 0 & 0 & 0 & S_{66} \end{bmatrix} \quad \cdots (15)$$

TETRAGONAL SYSTEM WITH LAUE SYMMETRY 4/m $$S = \begin{bmatrix} S_{11} & S_{12} & S_{13} & 0 & 0 & S_{16} \\ S_{12} & S_{11} & S_{13} & 0 & 0 & -S_{16} \\ S_{13} & S_{13} & S_{33} & 0 & 0 & 0 \\ 0 & 0 & 0 & S_{44} & 0 & 0 \\ 0 & 0 & 0 & 0 & S_{44} & 0 \\ S_{16} & -S_{16} & 0 & 0 & 0 & S_{66} \end{bmatrix} \quad \cdots (16)$$

FIG. 9

$$\sigma_{11} = \sigma_{22} = \sigma \qquad \cdots (17)$$

$$\sigma_{12} = \sigma_{13} = \sigma_{23} = \sigma_{33} = 0 \qquad \cdots (18)$$

$$\varepsilon^L_{33} = (S_{11} + S_{12} - 2S_{13})\, \sigma \sin^2 \psi + 2S_{13}\, \sigma$$
$$\cdots (19)$$

$$\sigma_{13} = \sigma_{23} = \sigma_{33} = 0 \qquad \cdots (20)$$

FIG. 10

When $\phi = 0°$ $$\varepsilon^L_{33}(0°) = \frac{1}{8}\{(6S_{11} + 2S_{12} - 8S_{13} + S_{66})\sigma_{11} + (2S_{11} + 6S_{12}$$
$$- 8S_{13} - S_{66})\sigma_{22} + (2S_{11} - 2S_{12} - S_{66})(\sigma_{11} - \sigma_{22})\cos 4\beta$$
$$- 2(S_{11} - 2S_{12} - S_{66})\sigma_{12}\sin 4\beta\}\sin^2\psi \qquad \cdots(21)$$
$$+ S_{13}(\sigma_{11} + \sigma_{22})$$

When $\phi = 90°$ $$\varepsilon^L_{33}(90°) = \frac{1}{8}\{(2S_{11} + 6S_{12} - 8S_{13} - S_{66})\sigma_{11} + (6S_{11} + 2S_{12}$$
$$- 8S_{13} + S_{66})\sigma_{22} - (2S_{11} - 2S_{12} - S_{66})(\sigma_{11} - \sigma_{22})\cos 4\beta$$
$$+ 2(S_{11} - 2S_{12} - S_{66})\sigma_{12}\sin 4\beta\}\sin^2\psi \qquad \cdots(22)$$
$$+ S_{13}(\sigma_{11} + \sigma_{22})$$

FIG. 11

When $\phi = 45°$ $$\varepsilon^L_{33}(45°) = S_{13}(\sigma_{11} + \sigma_{22}) + \frac{1}{8}\{4(S_{11} + S_{12} - 2S_{13})$$

$$(\sigma_{11} + \sigma_{22}) + 2(2S_{11} - 2S_{12} + S_{66})\sigma_{12}\cos 4\beta$$

$$+ 2(S_{11} - 2S_{12} + S_{66})(\sigma_{11} - \sigma_{22})\sin 4\beta\}\sin^2\psi \quad \cdots(23)$$

FIG. 12

When $\phi = 0°$ $$\frac{1}{\varepsilon^L_{33}(0°)} = \frac{1}{8}\{(6S_{11} + 2S_{12} - 8S_{13} + S_{66})\sigma_{11} + (2S_{11} + 6S_{12}$$
$$- 8S_{13} - S_{66})\sigma_{22} + (2S_{11} - 2S_{12} - S_{66})(\sigma_{11} - \sigma_{22})\cos 4\beta\} \quad \cdots(24)$$
$$\sin^2\psi + S_{13}(\sigma_{11} + \sigma_{22})$$

When $\phi = 90°$ $$\frac{1}{\varepsilon^L_{33}(90°)} = \frac{1}{8}\{(2S_{11} + 6S_{12} - 8S_{13} - S_{66})\sigma_{11} + (6S_{11} + 2S_{12}$$
$$- 8S_{13} + S_{66})\sigma_{22} - (2S_{11} - 2S_{12} - S_{66})(\sigma_{11} - \sigma_{22})\cos 4\beta\} \quad \cdots(25)$$
$$\sin^2\psi + S_{13}(\sigma_{11} + \sigma_{22})$$

FIG. 13

When $\phi = 45°$ $$\overline{\varepsilon^L_{33}(45°)} = S_{13}(\sigma_{11} + \sigma_{22}) + \frac{1}{8}\{4(S_{11} + S_{12} - 2S_{13})$$

$$(\sigma_{11} + \sigma_{22}) + 2(2S_{11} - 2S_{12} + S_{66})\sigma_{12}$$

$$+ 2(2S_{11} - 2S_{12} - S_{66})\sigma_{12}\cos 4\beta\}\sin^2\psi \quad \cdots(26)$$

FIG. 14

$$F1 = (\overline{\varepsilon^L_{33}(0°)} + \overline{\varepsilon^L_{33}(90°)})/2$$

$$= \frac{1}{2}(S_{11} + S_{12} - 2S_{13})(\sigma_{11} + \sigma_{22}) + S_{13}(\sigma_{11} + \sigma_{22}) \quad \cdots(27)$$

$$F2 = (\overline{\varepsilon^L_{33}(0°)} - \overline{\varepsilon^L_{33}(90°)})/2$$

$$= (\sigma_{11} - \sigma_{22})V \quad \cdots(28)$$

$$F3 = \overline{\varepsilon^L_{33}(45°)} - F1$$

$$= 2\sigma_{12} V \quad \cdots(29)$$

$$V = \frac{1}{8}\{2S_{11} - 2S_{12} + S_{66} + (2S_{11} - 2S_{12} - S_{66})\cos 4\beta\}\sin^2\psi \quad \cdots(30)$$

FIG. 16

| | (1) | (2) | (3) | (4) | (5) | (6) | (7) | (8) |
|---|---|---|---|---|---|---|---|---|
| $\phi=0°$ | $\beta$ | $-\beta$ | $-\beta+\frac{\pi}{2}$ | $\beta-\frac{\pi}{2}$ | $\beta+\frac{\pi}{2}$ | $-\beta-\frac{\pi}{2}$ | $-\beta+\pi$ | $\beta-\pi$ |
| $\phi=45°$ | $\beta-\frac{\pi}{4}$ | $-\beta-\frac{\pi}{4}$ | $-\beta+\frac{\pi}{4}$ | $\beta-\frac{3\pi}{4}$ | $\beta+\frac{\pi}{4}$ | $-\beta-\frac{3\pi}{4}$ | $-\beta+\frac{3\pi}{4}$ | $\beta-\frac{5\pi}{4}$ |
| $\phi=90°$ | $\beta-\frac{\pi}{2}$ | $-\beta-\frac{\pi}{2}$ | $-\beta$ | $\beta-\pi$ | $\beta$ | $-\beta-\pi$ | $-\beta+\frac{\pi}{2}$ | $\beta-\frac{3\pi}{2}$ |

FIG. 17

| hkl | $\psi$ (°) | $\beta$ (°) | $d_0$(nm) | $\theta_0$ (°) |
|---|---|---|---|---|
| 002 | 0.00 | 0.00 | 0.2078 | 21.76 |
| 011 | 46.81 | 0.00 | 0.2845 | 15.71 |
| 112 | 36.98 | 45.00 | 0.1668 | 27.50 |
| 022 | 46.81 | 0.00 | 0.1422 | 32.79 |
| 211 | 67.22 | 26.57 | 0.5151 | 28.60 |
| 111 | 56.42 | 45.00 | 0.2299 | 19.58 |
| 013 | 19.55 | 0.00 | 0.1305 | 36.16 |
| 222 | 56.42 | 45.00 | 0.1149 | 42.08 |
| 301 | 72.62 | 0.00 | 0.1241 | 38.36 |

STRESS MEASUREMENT METHOD USING X-RAY DIFFRACTION

The present application is a Continuation Application of U.S. application Ser. No. 10/650,059, now U.S. Pat. No. 6,874,369, filed Aug. 27, 2003.

BACKGROUND OF THE INVENTION

1. Field of the Invention

The present invention relates to a stress measurement method using X-ray diffraction. In particular, the present invention relates to a stress measurement method for a c-axis-oriented specimen of a tetragonal polycrystal.

2. Description of the Related Art

In general, a $\sin^2 \psi$ method has been used wish for the stress measurement method using X-ray diffraction. The $\sin^2 \psi$ method requires four conditions: (1) the crystal grain is small, (2) there is no strong preferred orientation, (3) a plane stress state is established within the depth of penetration of the X-ray, and (4) no stress gradient is present in the depth direction.

The stress measurement of a polycrystalline specimen, in which a specific crystal axis orients in a specific direction (such an orientation is referred to as a fiber texture), using the conventional $\sin^2 \psi$ method does not satisfy the above-described condition (2) including no strong preferred orientation. Therefore, the stress measurement of the fiber texture specimen using the $\sin^2 \psi$ method provides not a correct value but an approximate value.

With respect to such a fiber texture specimen, measurement methods more precise than the conventional $\sin^2 \psi$ method have been developed. Only for a fiber texture specimen of a cubic or hexagonal polycrystal, measurement methods more precise than the conventional $\sin^2 \psi$ method have been developed. For example, with respect to the cubic system, Tanaka, K., Ishihara, K. and Inoue, K., J. Soc. Mat. Sci., Japan, Vol. 45, No. 8, p. 945–950, 1996 discloses calculation formulae in a stress measurement method for the [111] fiber texture of a cubic polycrystal ([111] is perpendicular to the specimen surface). Besides, Tanaka, K., Akiniwa, Y., Ito, T. and Inoue, K., JSME International Journal, Series A, Vol. 42, No. 2, p. 224–234, 1998 discloses calculation formulae in a stress measurement method for the <111>, <100> and <110> fiber textures of a cubic polycrystal. With respect to the hexagonal system, Tanaka, K. and Akiniwa, Y., JSME International Journal, Series A, Vol. 41, No. 2, p. 287–289, 1998 discloses calculation formulae in a stress measurement method for the [001] fiber texture of a hexagonal polycrystal (only for an equi-biaxial stress state).

However, with respect to a fiber texture specimen of a tetragonal polycrystal (in this case, the c-axis of the tetragonal system is perpendicular to the specimen surface, the specimen being a c-axis-oriented specimen), no stress measurement method more precise than the conventional $\sin^2 \psi$ method has been developed. The stress measurement of the c-axis-oriented specimen of the tetragonal polycrystal is strongly desired in, for example, a semiconductor industry. Since there are many c-axis-oriented specimens in tetragonal specimens such as PZT, a stress measurement method for such specimens is desired.

SUMMARY OF THE INVENTION

Accordingly, it is an object of the present invention to provide a stress measurement method more precise than the conventional $\sin^2 \psi$ method for a c-axis-oriented specimen of a tetragonal polycrystal.

A first aspect of the present invention is a measurement method, in which a stress of a c-axis-oriented specimen of a tetragonal polycrystal is measured using X-ray diffraction under the assumption of a plane stress state. The target for the measurement is limited to the tetragonal system having the Laue symmetry 0.4/mmm. The method according to this aspect comprises the steps of: (a) preparing a c-axis-oriented specimen of a tetragonal polycrystal as a specimen to be measured; (b) defining, as a specimen coordinate system, a coordinate axis P3 perpendicular to a surface of the specimen and two coordinate axes P1 and P2 orthogonal to each other within the specimen surface, and arranging an X-ray optical system including an X-ray source and an X-ray detector within a plane including the coordinate axes P1 and P3; (c) selecting one set of Miller indices (hkl) of the specimen, and arranging the X-ray source and the X-ray detector to be symmetrical with a normal to a crystal plane with said one set of Miller indices (hkl), the normal to the crystal plane being inclined from a normal to the specimen surface at an angle of $\psi$, so that a diffracted X-ray from the crystal plane with said one set of Miller indices (hkl) can be detected with a diffraction angle $\theta_0$ (diffraction angle in a non-strain state); (d) irradiating the specimen with an X-ray, detecting the diffracted X-ray therefrom with the X-ray detector, adjusting the X-ray optical system to find out the diffraction angle $\theta$ at which the diffracted X-ray exhibits a maximum intensity, and determining the diffraction angle $\theta$ as a measurement value; (e) determining a strain through the use of the diffraction angle $\theta_0$ in the non-strain state and the diffraction angle $\theta$ measured; (f) selecting another Miller indices (hkl) of the specimen, repeating the above-described steps (c) to (e), and determining a strain with respect to said another set of Miller indices (hkl); (g) arranging the X-ray optical system including the X-ray source and the X-ray detector within a plane which is derived by rotation of the plane including the coordinate axes P1 and P3 around the coordinate axis P3 through an angle of $\phi=45°$; (h) repeating the above-described steps (c) to (f); (i) arranging the X-ray optical system including the X-ray source and the X-ray detector within a plane which is derived by rotation of the plane including the coordinate axes P1 and P3 around the coordinate axis P3 through an angle of $\phi=90°$; (j) repeating the above-described steps (c) to (f); and (k) determining a stress $\sigma_{11}$ in a direction of the coordinate axis P1, a stress $\sigma_{22}$ in a direction of the coordinate axis P2 and a shearing stress $\sigma_{12}$ between the coordinate axes P1 and P2 based on the strain $\epsilon(\phi=0°)$ determined in the above-described step (f), the strain $\epsilon(\phi=45°)$ determined in the above-described step (h), the strain $\epsilon(\phi=90°)$ determined in the above-described step (j) and $\sin^2 \psi$ through the use of stress calculation formulae determined under the conditions of a plane stress state and a symmetry 4/mmm.

A second aspect of the present invention is a measurement method, in which a stress of a c-axis-oriented specimen of a tetragonal polycrystal is measured using X-ray diffraction under the assumption of an equi-biaxial stress state. The targets for the measurement are both of the tetragonal system having the Laue symmetry 4/mmm and that having the Laue symmetry 4/m. The method according to this aspect comprises the steps of: (a) preparing a c-axis-oriented specimen of a tetragonal polycrystal as a specimen to be measured; (b) defining, as a specimen coordinate system, a coordinate axis P3 perpendicular to a surface of the specimen and two coordinate axes P1 and P2 orthogonal to each other within the specimen surface, and arranging an X-ray optical system including an X-ray source and an X-ray detector within an arbitrary plane including the coordinate axis P3; (c) selecting one set of Miller indices (hkl) of the specimen, and arranging the X-ray source and the X-ray detector to be symmetrical with a normal to a crystal plane with said one set of Miller indices (hkl), the normal to the crystal plane being inclined from a normal to the specimen surface at an angle of $\psi$, so that a diffracted X-ray from the crystal plane with said one set of Miller indices (hkl) can be detected with a diffraction angle $\theta_0$ (diffraction angle in a non-strain state); (d) irradiating the specimen with an X-ray, detecting the diffracted X-ray therefrom with the X-ray detector, adjusting the X-ray optical system to find out the diffraction angle $\theta$ at which the diffracted X-ray exhibits a maximum intensity, and determining the diffraction angle $\theta$ as a measurement value; (e) determining a strain through the use of the diffraction angle $\theta_0$ in the non-strain state and the diffraction angle $\theta$ measured; (f) selecting another set of Miller indices (hkl) of the specimen, repeating the above-described steps (c) to (e) and determining a strain with respect to said another set of Miller indices (hkl); (g) determining a plane stress $\sigma$ within the specimen surface based on the strain $\epsilon$ determined in the above-described step (f) and $\sin^2 \psi$ through the use of stress calculation formulae determined under the condition of an equi-biaxial stress state.

Materials belonging to the tetragonal system having the Laue symmetry 4/mmm include $BaTiO_3$, CuGaS2, $MgF_2$, $PbTiO_3$, $Mn_3O_4$, $MnF_2$, $MnO_2$, $TiO_2$ and $YVO_4$. Typical materials of the tetragonal system having the Laue symmetry 4/m include $PbMoO_4$ and $CaWO_4$.

According to the stress measurement method of the present invention, with respect to a c-axis-oriented specimen of a tetragonal polycrystal, more precise stress measurement can be performed as compared with that in the conventional $\sin^2 \psi$ method.

BRIEF DESCRIPTION OF THE DRAWINGS

FIG. 2 shows formulae (1) to (4) representing the principle of a stress measurement using X-ray diffraction;

FIG. 5 is a diagram showing a system of notation of an elastic compliance constant S, a stress $\sigma$ and a strain $\epsilon$ in the three coordinate systems;

FIG. 6 is a diagram showing the relationship between an elastic compliance constant in tensor notation and a 6×6 matrix in matrix notation;

FIG. 7 shows formulae (5) to (14) used for stress calculation;

FIG. 8 is a diagram showing elastic compliance constants of two types of tetragonal system in matrix notation;

FIG. 9 shows formulae (17) to (20) used for stress calculation;

FIG. 10 shows formulae (21) and (22) used for stress calculation;

FIG. 11 shows a formula (23) used for stress calculation;

FIG. 12 shows formulae (24) and (25) used for stress calculation;

FIG. 13 shows a formula (26) used for stress calculation;

FIG. 14 shows formulae (27) to (30) used for stress calculation;

FIG. 16 is a table showing angles of eight equivalent crystal coordinate systems;

FIG. 17 is a table showing the values of $\psi$, $\beta$, $d_0$ and $\theta_0$ with respect to each set of the Miller indices (hkl) of $PbTiO_3$.

DESCRIPTION OF THE PREFERRED EMBODIMENTS

Figure 1:
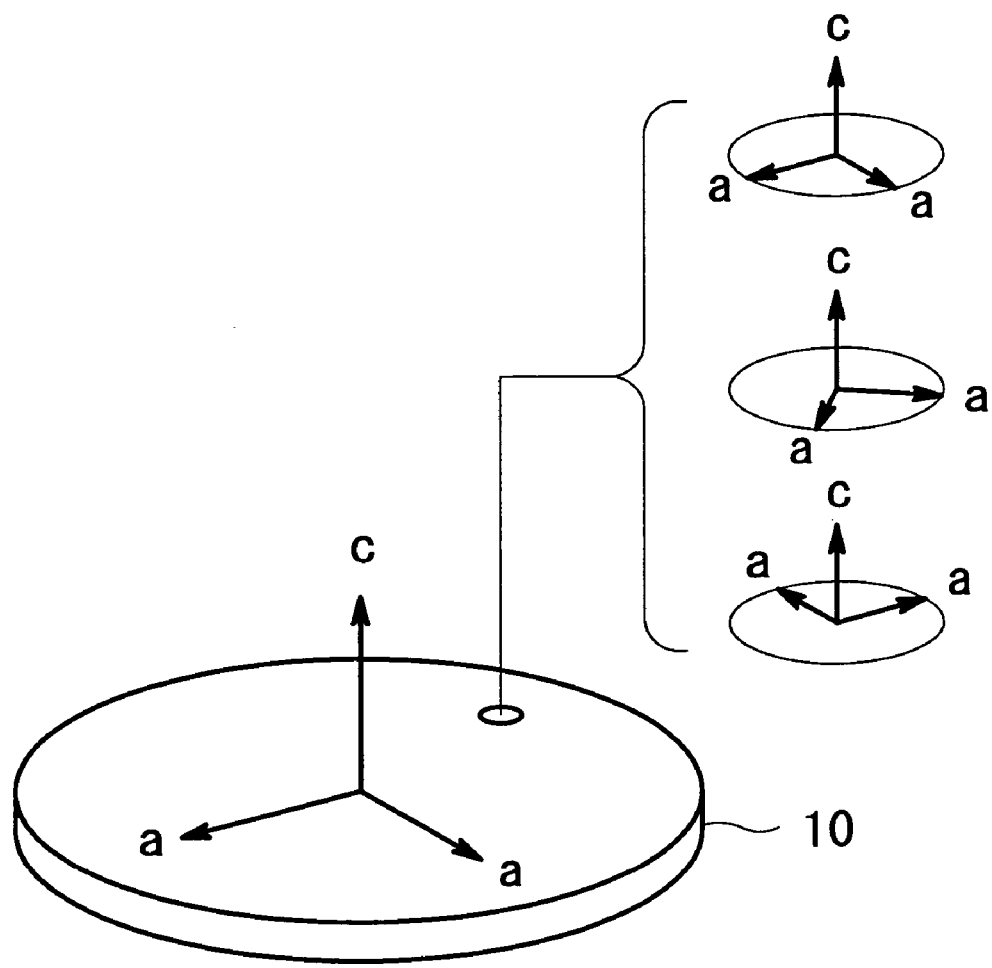
FIG. 1 is a perspective view for explaining a c-axis-oriented specimen of a tetragonal polycrystal.

Referring to FIG. 1 illustrating a c-axis-oriented specimen of a tetragonal polycrystal, most of many crystal grains which are present in the vicinity of the surface of a specimen 10 have the c-axes of the tetragonal system perpendicular to the specimen surface. The remaining two axes (since these are equivalent to each other, both axes are referred to as a-axes) of the crystal axes of the tetragonal system are present within a plane parallel to the specimen surface. With respect to the c-axis-oriented specimen, in general, directions of the two a-axes are random, and randomly oriented crystal grains are mixed with each other. Such a c-axis-oriented specimen is the target for measurement of the present invention.

The principle of the stress measurement using X-ray diffraction will be briefly described with reference to the formulae shown in FIG. 2. Formula (1) is the Bragg's equation representing the diffraction condition of X-ray. Under the assumption that the wavelength $\lambda$ (the wavelength of an X-ray used for the measurement) is constant, both sides of formula (1) are totally differentiated and transformed to become formula (2). On the other hand, the strain $\epsilon$ is defined by formula (3). When the Bragg's diffraction angle of a crystal plane in a non-strain state is represented by $\theta_0$, formula (4) is derived from formulae (2) and (3). That is, when the Bragg's diffraction angle $\theta_0$ in a non-strain state is known, the strain $\epsilon$ can be determined through measurement of the diffraction angle $\theta$ using X-ray diffraction. The above-described principle and the conventional $\sin^2 \psi$ method based thereon are described in detail in, for example, Jikkenbutsurigaku kouza 20, X-sen kaisetsu (Experimental physics course 20, X-ray diffraction), edited by Kohra, K., KYORITSU SHUPPAN CO., LTD., 1988, p. 571–575 "16.2 X-sen ouryokusokuteino genri (Principle of X-ray stress measurement)".

The general theory of the stress measurement method for a fiber texture specimen composed of a polycrystal which has a crystal system having three coordinate axes orthogonal to each other (tetragonal system, cubic system and the like) will be described.

Figure 3:
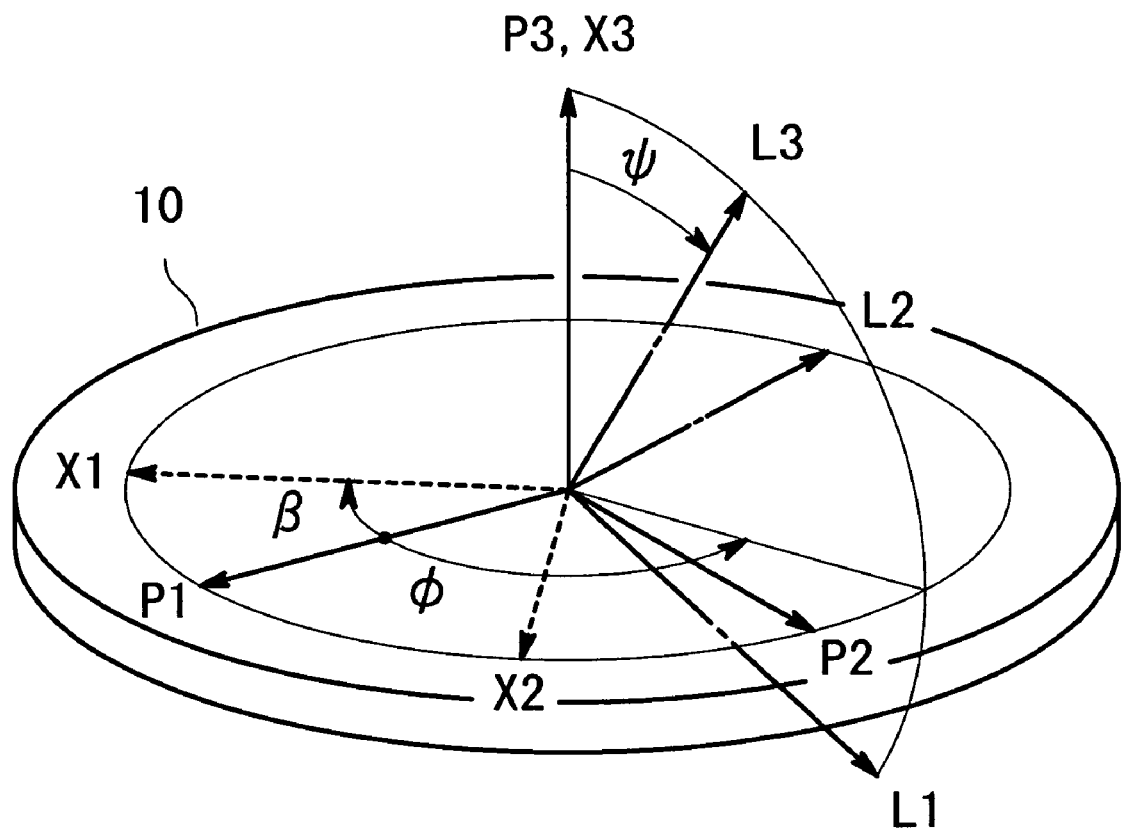
FIG. 3 is a perspective view showing three coordinate systems which will be used for explaining a calculation method in a stress measurement.

FIG. 3 is a perspective view showing three coordinate systems which will be used for explaining a calculation method in a stress measurement. With respect to a specimen 10 having a flat surface, three kinds of three-dimensional orthogonal coordinate systems are taken into consideration: a specimen coordinate system P, a crystal coordinate system X and a laboratory coordinate system L.

The specimen coordinate system P is a three-dimensional orthogonal coordinate system fixed on the specimen. Two coordinate axes P1 and P2 orthogonal to each other are defined within the surface of the specimen, and the coordinate axis P3 is set to become perpendicular to the specimen surface. The specimen coordinate system P is visible to the observer, and becomes a standard coordinate system to the observer. The stress applied to the specimen is determined with this specimen coordinate system.

The crystal coordinate system X is a three-dimensional orthogonal coordinate system representing crystal axes of a crystal grain to which the crystal plane contributing to the diffraction belongs, the crystal grain being present in the vicinity of the specimen surface. A fiber texture polycrystal is contemplated as the specimen and, therefore, a specific crystal axis (in this case, the coordinate axis X3) of every crystal grain contained in the specimen is perpendicular to the specimen surface. The other two coordinate axes X1 and X2 are present within the surface of the specimen. This crystal coordinate system X is not visible to the observer, and the coordinate axes X1 and X2 may point in a random direction. The crystal coordinate system X is derived by rotation of the specimen coordinate system P around the coordinate axis P3 in a counterclockwise direction through an angle of $\beta$ when viewed from the origin of P3 toward the forward of P3. As a matter of course, P3 and X3 coincide with each other.

The laboratory coordinate system L is based on an X-ray optical system in the X-ray diffraction measurement. The laboratory coordinate system L is derived in a manner that the specimen coordinate system P is rotated around the coordinate axis P3 in a clockwise direction through an angle of $\phi$ when viewed from the origin of P3 toward the forward of P3 and, in addition, P3 and P1 are rotated around P2 at that time (P2 is present in the location of L2 shown in FIG. 3) through an angle of $\psi$. The direction of L3 is the direction of the normal to the crystal plane contributing to the diffraction. This laboratory coordinate system L is used for measuring the diffraction angle (that is, for measuring the strain).

A system of notation of an elastic compliance constant S, a stress $\sigma$ and a strain $\epsilon$ in each of the coordinate systems is shown in FIG. 5. The strain $\epsilon_{ij}$ (i, j=1, 2, 3) and the stress $\sigma_{ij}$ (i, j=1, 2, 3) are 3×3 matrices. The elastic compliance constant $S_{ijkl}$ (i, j, k, l=1, 2, 3) is in tensor notation.

There is a relationship shown in FIG. 6 between the elastic compliance constant $S_{ijkl}$ (i, j, k, l=1, 2, 3) in tensor notation and the 6×6 matrices $S_{pq}$ (p, q=1, 2, 3, 4, 5, 6) in matrix notation. For example, $S_{1213}$ is equal to a quarter of $S_{65}$.

Figure 4:
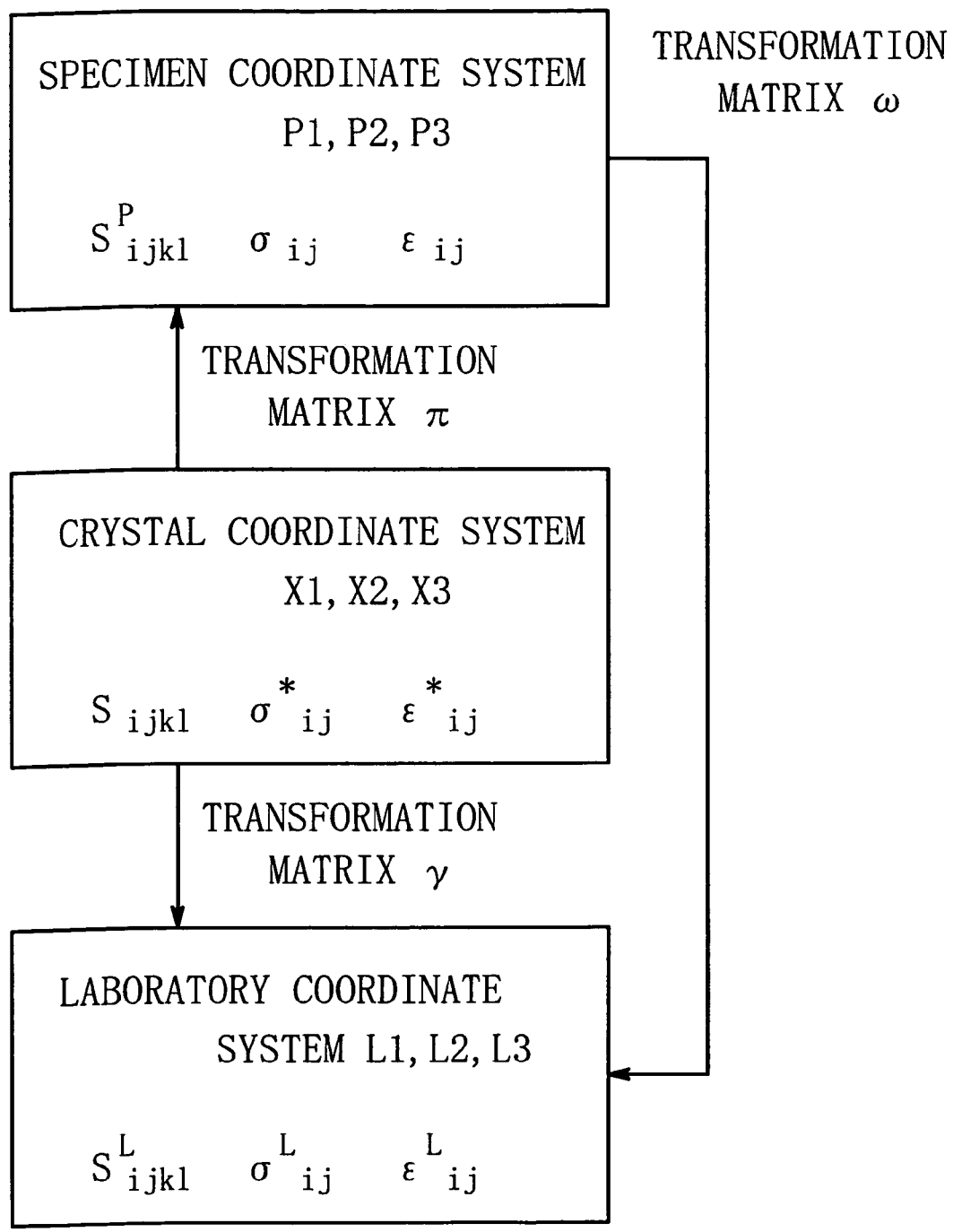
FIG. 4 is a diagram for explaining transformation matrices $\pi$, $\omega$ and $\gamma$ between the three coordinate systems.

When transformation matrices $\pi$, $\omega$ and $\gamma$ between three coordinate systems are defined as shown in FIG. 4, these transformation matrices can be represented by formulae (5) to (7) shown in FIG. 7. These formulae can be represented using a rotation matrix R1($\delta$) which rotates around a coordinate axis 1 through an angle of $\delta$, a rotation matrix R2($\delta$) which rotates around a coordinate axis 2 through an angle of $\delta$ and a rotation matrix R3($\delta$) which rotates around a coordinate axis 3 through an angle of $\delta$. The forms of the rotation matrices R1 to R3 are represented by formulae (8) to (10) as shown in FIG. 7.

On the other hand, there are relationships represented by formulae (11) to (13) shown in FIG. 7 between the strain $\epsilon$ and the stress $\sigma$. Formula (14) is derived from formulae (11) to (13). In this formula (14), the strain $\epsilon^L_{33}$ (measurable value) in the laboratory coordinate system is represented by the elastic compliance constant S in the crystal coordinate system, the load stress $\sigma$ in the specimen coordinate system and transformation matrices.

The above description is the general theory of the stress measurement method for the fiber texture specimen. These are also described in the above-described Tanaka, K., Akiniwa, Y., Ito, T. and Inoue, K., JSME International Journal, Series A, Vol. 42, No. 2, p. 224–234, 1998.

Next, the property specific to the tetragonal system, that is, the characteristic items of the present invention, will be described. The tetragonal system can be classified based on the symmetry thereof, and be classified into the two types: the Laue symmetry (that is, the symmetry of the reciprocal lattice space) 4/mmm and that having the Laue symmetry 4/m. The former includes a four-fold symmetry about the c-axis and three mirror symmetries and, therefore, has high symmetry. The latter includes a four-fold symmetry about the c-axis and one mirror symmetry and, therefore, has low symmetry. The symmetry of the crystal is described in, for example, X-sen kesshoukaisekino tebiki, Ouyoubutsurigaku sensho (Guide to X-ray crystal analysis, Applied physics sampler), Sakurai, T., Shokabou, 1983, p. 53.

The single-crystal elastic compliance constant S of the tetragonal system belonging to 4/mmm can be represented by formula (15) shown in FIG. 8. On the other hand, the single-crystal elastic compliance constant S of the tetragonal system belonging to 4/m can be represented by formula (16) shown in FIG. 8.

Next, two types of stress state are assumed with respect to such a tetragonal system, and each stress state will be ascertained whether the stress can be measured using X-ray diffraction, that is, whether the stress can be experimentally determined based on the relationship between the measured value of the strain $\epsilon$ and the measurement conditions of $\psi$ and the like.

First, an "equi-biaxial stress state" is assumed. This is a stress state in which formulae (17) and (18) as shown in FIG. 9 hold good. That is, with respect to specimen coordinate system P, the stress $\sigma_{11}$ in the direction of the coordinate axis P1 is equal to the stress $\sigma_{22}$ in the direction of the coordinate axis P2, equal stress, and the shearing stress $\sigma_{12}$ between the coordinate axes P1 and P2 is zero in this state. No stress is applied in the direction perpendicular to the specimen surface (the direction of the coordinate axis P3) because the specimen surface is a free surface. Accordingly, $\sigma_{13}$, $\sigma_{23}$ and $\sigma_{33}$ are zero. Under such a stress condition, formula (15) shown in FIG. 8 representing the elastic compliance constant is substituted into formula (14) shown in FIG. 7 and, thereby, formula (19) shown in FIG. 9 is derived. Likewise, under the same stress condition, formula (16) shown in FIG. 8 representing the elastic compliance constant is substituted into formula (14) shown in FIG. 7 and, thereby, formula (19) shown in FIG. 9 is derived too.

In this manner, under the equi-biaxial stress state, the stress can be measured based on formula (19) shown in FIG. 9 with respect to both of the tetragonal system belonging to 4/mmm and 4/m. That is, when the strain $\epsilon^L_{33}$ and $\sin^2 \psi$ are plotted on a graph, there is a substantially linear relationship therebetween and, thereby, the slope can be determined. The stress $\sigma$ can be calculated through the use of the resulting slope and the elastic compliance constants $S_{11}$, $S_{12}$ and $S_{13}$ of the crystal.

In general, it is believed that a c-axis-oriented specimen of the tetragonal system is not in the equi-biaxial stress state, which is the specific stress state, but in the plane stress state described below. Therefore, when the stress measurement based on formula (19) shown in FIG. 9 cannot be satisfactorily performed (no linear relationship is observed in the above-described graph), the stress must be determined under the assumption of a more general plane stress state, as described below.

Consequently, the "plane stress state" is assumed next. This is a stress state in which formula (20) shown in FIG. 9 holds good. That is, with respect to the specimen coordinate system P, the stress $\sigma_{11}$ in the direction of the coordinate axis P1 is different from the stress $\sigma_{22}$ in the direction of the coordinate axis P2, non-equal stress, and the shearing stress $\sigma_{12}$ between the coordinate axes P1 and P2 is present. No stress is applied in the direction perpendicular to the specimen surface (the direction of the coordinate axis P3), because the specimen surface is a free surface). Accordingly, $\sigma_{13}$, $\sigma_{23}$ and $\sigma_{33}$ are zero. Under such a stress condition, the calculation result of the tetragonal system having the Laue symmetry 4/mmm is different from that of the Laue symmetry 4/m. In conclusion, with respect to the tetragonal system belonging to 4/mmm, the calculation result can be satisfactorily organized, and formulae suitable for the stress measurement are available. On the other hand, with respect to the tetragonal system belonging to 4/m, no formula suitable for the stress measurement is currently available. Consequently, according to the present invention, with respect to the "plane stress state" (general stress state of the specimen surface), the stress of the tetragonal system having only the Laue symmetry 4/mmm can be measured.

With respect to the tetragonal system having the Laue symmetry 4/mmm, formula (15) shown in FIG. 8 representing the elastic compliance constant is substituted into formula (14) shown in FIG. 7 based on formula (20) shown in FIG. 9 representing the "plane stress state". Furthermore, the crystal plane strains $\epsilon^L_{33}$ are determined with respect to $\phi=0°$, $45°$ and $90°$ and, thereby, formulae (21) and (22) shown in FIG. 10 and formula (23) shown in FIG. 11 are derived. However, the present forms of these formulae are not suitable for the stress measurement.

Figure 15:
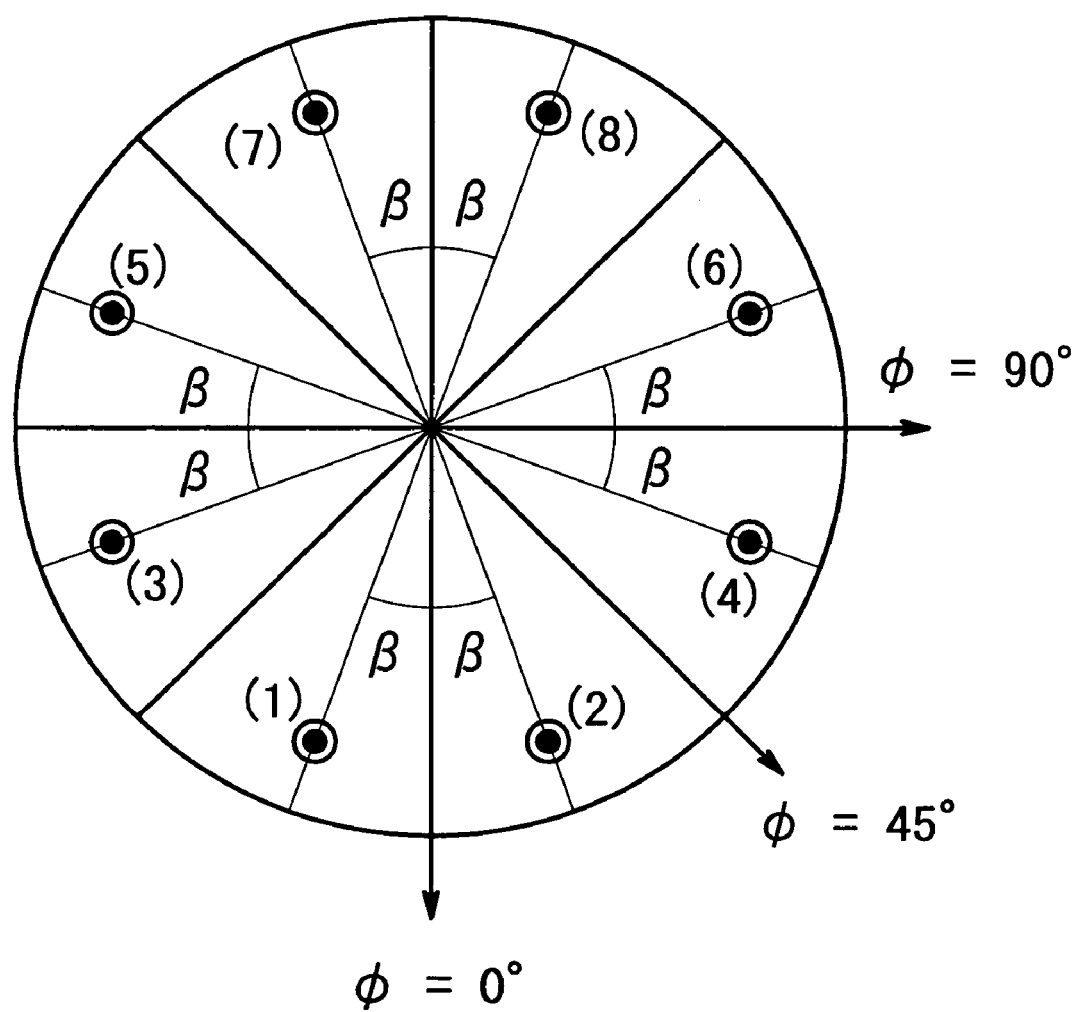
FIG. 15 is a diagram showing the symmetrical property of the Laue symmetry 4/mmm.

Then, the symmetry 4/mmm will be discussed. FIG. 15 is a diagram showing the symmetrical property of the tetragonal system having the Laue symmetry 4/mmm, viewed from the c-axis direction. The symmetry viewed from the c-axis direction, the symmetry relating to the present invention, is composed of a combination of a four-fold symmetry about the c-axis and one mirror symmetry. Here, $\phi=0°$, $45°$ and $90°$ are set at the locations shown in FIG. 15. An X-ray optical system is arranged in the location indicated by $\phi$. It is assumed that when the X-ray optical system is set in the location of $\phi=0°$, diffracted rays from a group of crystal grains having the crystal coordinate system represented by the point (1) rotated through an angle of $\beta$ from the location of $\phi=0°$ are detected. In this case, diffracted rays from a group of crystal grains having eight equivalent crystal coordinate systems indicated by (1) to (8) shown in FIG. 15 are simultaneously detected. Consequently, the detected diffracted X-ray is an average value of the diffracted rays from a group of crystal grains having these eight types of equivalent crystal coordinate systems. The angle of each of the crystal coordinate systems (1) to (8) relative to the location of $\phi=0°$ is described in a row $\phi=0°$ in the table shown in FIG. 16.

Referring back to formula (21) shown in FIG. 10, this formula shows a strain corresponding to one reflection (one crystal plane) with respect to $\phi=0°$. However, eight reflections (eight crystal planes) from different crystal grains are actually present based on the above-described symmetry, and are simultaneously measured. Consequently, strains must be determined by independently substituting eight angles described in the row $\phi=0°$ shown in FIG. 16 into $\beta$ in formula (21), and the average thereof is the strain actually measured. In the calculation of the above-described average value, the terms of $\sin 4\beta$ cancel each other to become zero, and the terms of $\cos 4\beta$ remain as a term of $\cos 4\beta$ with no change. The result of the calculation is formula (24) shown in FIG. 12. In this formula (24), a horizontal line drawn above $\epsilon^L_{33}(0°)$ refers to "an average value" of the above-described eight types of reflection.

Likewise, with respect to $\phi=90°$, eight angles described in the row $\phi=90°$ shown in FIG. 16 are independently substituted into formula (22) shown in FIG. 10, and the average value thereof is determined, so that formula (25) shown in FIG. 12 is derived.

With respect to $\phi=45°$, eight angles described in the row $\phi=45°$ shown in FIG. 16 are independently substituted into formula (23) shown in FIG. 11, and the average value thereof is determined, so that formula (26) shown in FIG. 13 is derived.

The three formulae (24) to (26) determined as described above are combined with each other, followed by transformation, and formulae (27) to (30) shown in FIG. 14 are thereby derived. Here, V in formulae (28) and (29) is represented by formula (30).

The stress measurement can be performed through the use of these formulae as described below. Referring to formula (27) shown in FIG. 14, an X-ray optical system is set in the location of $\phi=0°$, and X-ray diffraction measurement is performed with respect to a plurality of $\psi$ (that is, with respect to a plurality of Miller indices), diffracted rays from which can be detected, so that each diffraction angle $\theta$ is measured. With respect to each $\psi$, a strain $\epsilon$ is calculated from the diffraction angle $\theta$ and the diffraction angle $\theta_0$ (known) in a non-strain state. The resulting strain $\epsilon$ corresponds to an average value of $\epsilon^L_{33}(0°)$ Likewise, the X-ray diffraction measurement is performed with respect to $\phi=90°$ in a manner similar to that described above, and an average of $\epsilon^L_{33}(90°)$ is determined with respect to each $\psi$. These are plotted on a graph. That is, the horizontal axis indicates $\sin^2\psi$, the vertical axis indicates F1 (that is, one-half the sum of the strain at $\phi=0°$ and the strain at $\phi=90°$), each measurement value is plotted, and an approximate linear line of the resulting graph is determined, for example, a regression line is determined by a least-squares method. The value of $\sigma_{11}+\sigma_{22}$ can be determined from the slop of the resulting linear line and the elastic compliance constants $S_{11}$, $S_{12}$, and $S_{13}$.

Likewise, with respect to formula (28), the horizontal axis indicates V, see formula (34), the vertical axis indicates F2 (that is, one-half the difference between the strain at $\phi=0°$ and the strain at $\phi=90°$), each measurement value is plotted, and an approximate linear line of the resulting graph is determined. The slop of the resulting linear line corresponds to $\sigma_{11}-\sigma_{22}$.

Since the value of $\sigma_{11}+\sigma_{22}$ and the value of $\sigma_{11}-\sigma_{22}$ are obtained, $\sigma_{11}$, and $\sigma_{22}$ can be calculated from them. In this manner, the strain $\sigma_{11}$ in the direction of the coordinate axis P1 and the strain $\sigma_{22}$ in the direction of the coordinate axis P2 are determined.

Next, with respect to formula (29), the horizontal axis indicates V, the vertical axis indicates F3 (that is, the value determined by subtracting the above-described F1 from the strain at $\phi=45'$), each measurement value is plotted, and an approximate linear line of the resulting graph is determined. The slop of the resulting linear line corresponds to $2\sigma_{12}$.

Next, a specific procedure of the stress measurement will be described in consideration of an actual specimen. With respect to the specimen to be measured, $PbTiO_3$ is assumed as the tetragonal polycrystal specimen having the Laue symmetry 4/mmm. With respect to the lattice constant thereof, a=0.3902 nm and b=0.4156 nm. The space group is 99 (P4 mm). With respect to the elastic compliance constant (in unit of 1/TPa) thereof, $S_{11}=7.12$, $S_{12}=-2.1$, $S_{33}=32.5$, $S_{44}=12.2$ and $S_{66}=7.9$. The values of such an elastic compliance constant are known (described in a book, a literature, or the like regarding physical properties of various substances).

Figure 18:
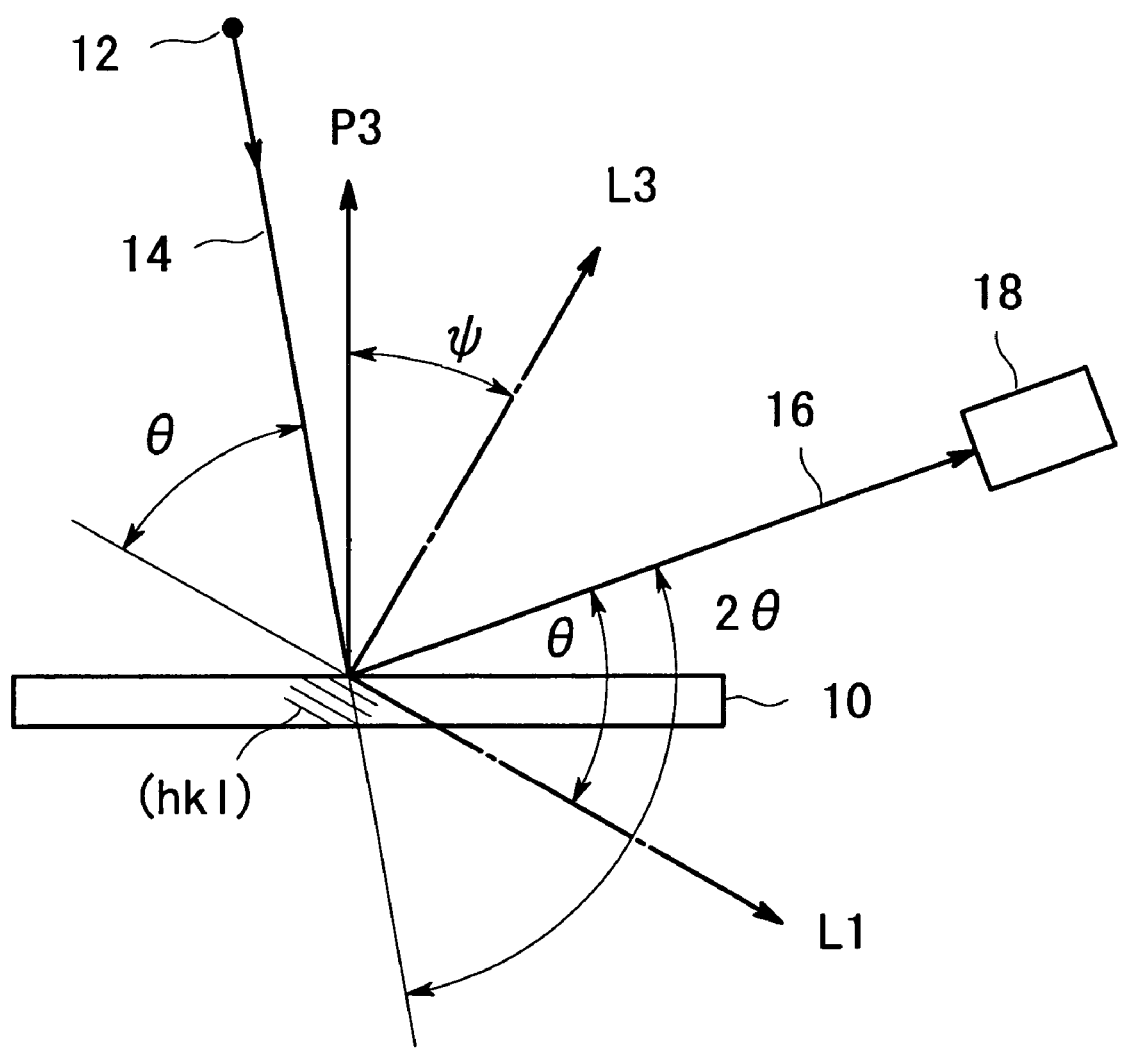
FIG. 18 is a diagram for explaining an X-ray optical system.

With respect to $PbTiO_3$, the Miller indices (hkl), the diffracted ray from which can be measured, include those shown in FIG. 17. The direction of the normal to the crystal plane represented by the Miller indices (hkl) is the direction inclined at an angle of ψ from the direction of the normal to the specimen surface (that is, from the direction of the coordinate axis P3) as shown in FIG. 18. The value of ψ with respect to each Miller indices is as shown in FIG. 17. With respect to each Miller indices, the value of β, the lattice spacing $d_0$ in a non-strain state and the Bragg's angle $θ_0$ corresponding thereto are also shown in FIG. 17. The Bragg's angle $θ_0$ is calculated from $d_0$ under the assumption that a CuKα ray (wavelength λ=0.154056 nm) is used.

First of all, an X-ray optical system is set in the location of φ=0° shown in FIG. 3. That is, the L3-L1 plane (a plane including the coordinate axes L3 and L1) in the laboratory coordinate system is made to coincide with the P1-P3 plane in the specimen coordinate system. FIG. 18 is a diagram showing a state in which the L3-L1 plane in the laboratory coordinate system is made parallel to the paper surface. The direction of the normal to the crystal plane with the Miller indices (hkl) is the direction of the coordinate axis L3, and is inclined at an angle of ψ from the coordinate axis P3. The crystal plane with the Miller indices (hkl) is parallel to the coordinate axis L1. The X-ray 14 incident on the specimen 10 from the X-ray source 12 is diffracted at the crystal plane with the Miller indices (hkl), and the resulting diffracted X-ray 16 is detected with the X-ray detector 18. The X-ray source 12 and the X-ray detector 18 is arranged to be symmetrical with the normal to the crystal plane with the Miller indices (hkl). The incident X-ray 14 and the crystal plane form an angle of θ, and the diffracted X-ray 16 and the crystal plane form an angle of θ as well.

When the Miller indices (hkl) are determined, the Bragg's angle $θ_0$ in a non-strain state is thereby determined (known). Therefore, the X-ray source 12 and the X-ray detector 18 are adjusted within the range of a very small angle in the vicinity of this $θ_0$ so that a diffraction angle θ at which the intensity of the diffracted x-ray becomes a maximum can be found out. This value θ is taken as a measurement value. A strain ε can be calculated from the difference between this measurement value θ and the Bragg's angle $θ_0$. In this manner, strains ε (=0°) are determined with respect to a plurality of Miller indices (hkl), that is, with respect to a plurality of ψ. It is noted that when a one-dimensional or two-dimensional position-sensitive X-ray detector is used as the above-described X-ray detector 18, the adjustment (scanning) of the X-ray detector 18 becomes correspondingly unnecessary.

Next, the X-ray optical system is set in the location of φ=45°, a similar measurement is performed and, therefore, a strain ε (φ=45°) can be determined with respect to each ψ. Furthermore, the X-ray optical system is set in the location of φ=90°, a similar measurement is performed and, therefore, a strain ε (φ=90°) can be determined with respect to each ψ.

In this manner, the strain ε corresponding to each ψ is determined with respect to φ=0°, 45° and 90°. Consequently, $sin^2ψ$ or V and the value of F1, F2 or F3 are plotted on a graph, the slope of an approximate linear line is determined, and $σ_{11}$, $σ_{22}$ and $σ_{12}$ can be calculated from the slops based on formulae (27) to (30) shown in FIG. 14. The value of β used for the calculation is the value shown in FIG. 17, and the values of the elastic compliance constants $S_{11}$, $S_{12}$, $S_{13}$ and $S_{66}$ are as described above.

The above description is the specific procedure of the stress measurement method under the assumption of the plane stress state. However, the specific procedure of the stress measurement method under the assumption of the equi-biaxial stress state is simpler, as described below.

With respect to the formulae, only formula (19) shown in FIG. 9 is used. The stress to be determined is one kind, that is, $σ_{11}=σ_{22}=σ_{12}$. An X-ray optical system is set in an arbitrary plane including the coordinate axis P3 (any plane can be selected because of the equi-biaxial stress state), and X-ray diffraction measurement is performed with respect to a plurality of ψ, diffracted rays from which can be detected, so that each diffraction angle θ is measured. With respect to each ψ, strain ε is calculated from the diffraction angle θ and the diffraction angle $θ_0$ (known) in a non-strain state. The results are plotted while the horizontal axis indicates $sin^2ψ$, and the vertical axis indicates $ε^L_{33}$. An approximate linear line of the resulting graph is determined, for example, a regression line is determined by a least-squares method. The value of σ can be determined from the slop of the resulting linear line and the elastic compliance constants $S_{11}$, $S_{12}$, and $S_{13}$.

What is claimed is:

1. A stress measurement method using X-ray diffraction, said method comprising:
   (a) preparing a c-axis-oriented specimen of a tetragonal polycrystal as a specimen to be measured;
   (b) defining, as a specimen coordinate system, a coordinate axis P3 perpendicular to a surface of the specimen and two coordinate axes P1 and P2 orthogonal to each other within the specimen surface, and arranging an X-ray optical system including an X-ray source and an X-ray detector such that a coordinate axis L3 of a laboratory coordinate system based on the X-ray optical system is within a plane including the coordinate axes P1 and P3;
   (c) selecting one set of Miller indices (hkl) of the specimen, and arranging the X-ray source and the X-ray detector to be symmetrical about a normal to a crystal plane with said one set of Miller indices (hkl), the normal to the crystal plane being inclined from a normal to the specimen surface at an angle of ψ, so that a diffracted X-ray from the crystal plane with said one set of Miller indices (hkl) is detectable with a diffraction angle $θ_0$ (diffraction angle in a non-strain state);
   (d) irradiating the specimen with an X-ray, detecting a diffracted X-ray therefrom with the X-ray detector, adjusting the X-ray optical system to determine a diffraction angle θ at which the diffracted X-ray exhibits a maximum intensity, and determining the diffraction angle θ as a measurement value;
   (e) determining a strain based on the diffraction angle $θ_0$ in the non-strain state and the measured diffraction angle θ;
   (f) repeating steps (c) to (e) in which another set of Miller indices (hkl) is selected in step (c), and determining a strain with respect to said another set of Miller indices (hkl);
   (g) arranging said coordinate axis L3 of the laboratory coordinate system within a plane which is derived by rotating the plane including the coordinate axes P1 and P3 around the coordinate axis P3 through an angle of φ=45';
   (h) repeating steps (c) to (f);

(i) arranging said coordinate axis L3 of the laboratory coordinate system within a plane which is derived by rotating the plane including the coordinate axes P1 and P3 around the coordinate axis P3 through an angle of $\phi=90°$;

(j) repeating steps (c) to (f); and (k) determining a stress $\sigma_{11}$ in a direction of the coordinate axis P1, a stress $\sigma_{22}$ in a direction of the coordinate axis P2 and a shearing stress $\sigma_{12}$ between the coordinate axes P1 and P2 based on a strain $\epsilon(\phi=0°)$ determined in step (f), a strain $\epsilon(\phi=45°)$ determined in step (h), a strain $\epsilon(\phi=90°)$ determined in step (j) and $\sin^2\psi$ based on stress calculation formulae determined under conditions of a plane stress state and a symmetry 4/mmm.

2. A stress measurement method using X-ray diffraction, said method comprising:

(a) preparing a c-axis-oriented specimen of a tetragonal polycrystal as a specimen to be measured;

(b) defining, as a specimen coordinate system, a coordinate axis P3 perpendicular to a surface of the specimen and two coordinate axes P1 and P2 orthogonal to each other within the specimen surface, and arranging an X-ray optical system including an X-ray source and an X-ray detector such that a coordinate axis L3 of a laboratory coordinate system based on the X-ray optical system is within a plane including the coordinate axis P3;

(c) selecting one set of Miller indices (hkl) of the specimen, and arranging the X-ray source and the X-ray detector to be symmetrical about a normal to a crystal plane with said one set of Miller indices (hkl), the normal to the crystal plane being inclined from a normal to the specimen surface at an angle of $\psi$, so that a diffracted X-ray from the crystal plane with said one set of Miller indices (hkl) is detectable with a diffraction angle $\theta_0$ (diffraction angle in a non-strain state);

(d) irradiating the specimen with an X-ray, detecting a diffracted X-ray therefrom with the X-ray detector, adjusting the X-ray optical system to determine a diffraction angle $\theta$ at which the diffracted X-ray exhibits a maximum intensity, and determining the diffraction angle $\theta$ as a measurement value;

(e) determining a strain based on the diffraction angle $\theta_0$ in the non-strain state and the measured diffraction angle $\theta$;

(f) repeating steps (c) to (e) in which another set of Miller indices (hkl) is selected in step (c), and determining a strain with respect to said another set of Miller indices (hkl);

(g) determining a plane stress $\sigma$ within the specimen surface based on a strain $\epsilon$ determined in the above-described step (f) and $\sin^2\psi$ based on stress calculation formulae determined under a condition of an equibiaxial stress state.

* * * * *